United States Patent
Morrison et al.

(10) Patent No.: US 6,676,964 B2
(45) Date of Patent: Jan. 13, 2004

(54) METHOD FOR DETERMINING THE THREE-DIMENSIONAL STRUCTURE OF A PROTEIN

(75) Inventors: Dennis R. Morrison, Kemah, TX (US); Benjamin Mosier, Houston, TX (US)

(73) Assignee: The United States of America as represented by the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/774,168

(22) Filed: Jan. 26, 2001

(65) Prior Publication Data
US 2001/0026812 A1 Oct. 4, 2001

Related U.S. Application Data

(60) Division of application No. 09/079,766, filed on May 15, 1998, now Pat. No. 6,387,399, which is a continuation-in-part of application No. 08/349,169, filed on Dec. 2, 1994, now Pat. No. 5,827,531.

(51) Int. Cl.[7] .............................. A61K 9/48; A61K 9/16; A61K 9/50; B01J 13/02; B65B 1/00; G01N 31/00; G01N 19/00
(52) U.S. Cl. ...................... 424/451; 424/491; 264/4.32; 264/4.33; 702/27
(58) Field of Search ................................ 424/451, 491; 264/4.32, 4.33; 702/27

(56) References Cited

PUBLICATIONS

Punzi, J.S. et al., "Protein crystal growth in the presence of poly(vinylidene difluoride) membrane", J. Appl. Cryst., vol. 24, pp. 406–408 (1991).*

* cited by examiner

Primary Examiner—Jeffrey Fredman
Assistant Examiner—Teresa Strzelecka
(74) Attorney, Agent, or Firm—James M. Cate

(57) ABSTRACT

Microcapsules prepared by encapsulating an aqueous solution of a protein, drug or other bioactive substance inside a semi-permeable membrane by are disclosed. The microcapsules are formed by interfacial coacervation under conditions where the shear forces are limited to 0–100 dynes/cm$^2$ at the interface. By placing the microcapsules in a high osmotic dewatering solution, the protein solution is gradually made saturated and then supersaturated, and the controlled nucleation and crystallization of the protein is achieved. The crystal-filled microcapsules prepared by this method can be conveniently harvested and stored while keeping the encapsulated crystals in essentially pristine condition due to the rugged, protective membrane. Because the membrane components themselves are x-ray transparent, large crystal-containing microcapsules can be individually selected, mounted in x-ray capillary tubes and subjected to high energy x-ray diffraction studies to determine the 3-D structure of the protein molecules. Certain embodiments of the microcapsules of the invention have composite polymeric outer membranes which are somewhat elastic, water insoluble, permeable only to water, salts, and low molecular weight molecules and are structurally stable in fluid shear forces typically encountered in the human vascular system.

8 Claims, 8 Drawing Sheets

METHOD FOR DETERMINING THE THREE-DIMENSIONAL STRUCTURE OF A PROTEIN

This application is a divisional of U.S. Patent Application No. 09/079,766 filed May 15, 1998, now U.S. Pat. No. 6,387,399, which is a continuation-in-part of U.S. Patent Application No. 08/349,169 filed Dec. 2, 1994, now U.S. Pat. No. 5,827,531.

STATEMENT REGARDING FEDERALLY SPONSORED RESEARCH OR DEVELOPMENT

The invention described herein was made in the performance of work under a NASA contract and is subject to Public Law 96-517(35 U.S.C. § 200 et seq.). The contractor has not elected to retain title to the invention.

BACKGROUND OF THE INVENTION

1. Field of the Invention

The present invention generally relates to methods of microencapsulating bioactive substances, and particularly to methods utilizing interfacial coacervation at the immiscible interface of two liquid phases. More particularly, the invention pertains to such methods which maintain conditions of low shear force during formation of the microcapsules. The present invention also pertains to microcapsules formed by such methods and to their methods of use.

2. Description of the Prior Art

Liquid microcapsules and liposomes are often used to store and deliver bioactive substances such as drugs, enzymes or biocatalysts. One recent effort to provide liposomes with enhanced circulation times is that disclosed in U.S. Pat. No. 5,013,556 to Woodle et al. Liposomes created by Woodle et al. contain 1–20 mole % of an amphipathic lipid derivatized with a polyalkylether (such as phosphatidyl ethanolamine derivitized with polyethyleneglycol). Another improvement is provided by U.S. Pat. No. 5,225,212 (issued to Martin et al.) which discloses a liposome composition for extended release of a therapeutic compound into the bloodstream. Those liposomes are composed of vesicle-forming lipids derivatized with a hydrophilic polymer, wherein the liposome composition is used for extending the period of release of a therapeutic compound such as a polypeptide, injected within the body. Formulations of "stealth" liposomes have also been created with lipids that are less detectable by immune cells in an attempt to avoid phagocytosis (Allen et al. (1992) *Cancer Res.* 52:2431–39.) Still other modifications of lipids (i.e., neutral glycolipids) may be made in order to produce anti-viral formulations. U.S. Pat. No. 5,192,551 to Willoughby et al. 1993. However, new types of liposomes and microcapsules are needed to exploit the various unique applications of this type of drug delivery.

Many proteins of interest, such as those containing bioactive drug sites or enzymatically active sites, are only slightly soluble in aqueous solutions, which limits the quantity of drug that can be microencapsulated by usual techniques. In an effort to increase the amount of drug delivered to the target tissues, crystalline drug suspensions are sometimes encapsulated. Fragile liposome or non-lipid carriers too often rupture or are pierced by the sharp crystals, however, leading to loss of the drug before it reaches its target. This undesired release of the drug crystals has also been known to damage the lining of blood vessels.

Others have endeavored to increase the amount of drug in a liposome by loading the drug into the liposome by via a pH gradient. U.S. Pat. No. 5,192,549 (issued to Barenolz and Haran) describes methods for forming liposomes and then obtaining transmembrane loading of amphiphatic drugs into the liposomes using an ammonium ion gradient between the internal and external aqueous phase on either side of the liposome membrane. The movement of ammonium from inside the liposome to the outside causes a pH change inside, thereby creating a driving force for the amphiphatic drug to be loaded or released through the membrane. Disadvantages of this method are that it requires the encapsulation of ammonium sulfate or another ammonium salt inside the liposomes, and transmembrane transport is limited to weak amphiphatic compounds. This type of drug concentrating method has not been used successfully to form encapsulated crystals, however. If this method were applied to protein crystal growth inside the liposome, it would be limited to applications where the protein was compatible with the ammonium salts and dissolved $NH_4$.

Another area where protein crystals are used is in macromolecular crystallography, which requires large, high-quality protein crystals. Conventional methods of growing protein crystals, as required for x-ray diffraction studies of three-dimensional structure, are often compromised by the formation of multiple small crystals, amorphous precipitates and aggregates rather than a single, or a few, large crystals from the limited amount of protein in the available mother liquor. It has been estimated that about $10^{15}$ molecules are required to make up a crystal of sufficient size for x-ray crystallographic examination (Proteins Structures and Molecular Properties, 2nd Ed., Thomas E. Creighton, Ed., W. H. Freeman and Co., NY, N.Y., p. 203). It is often observed that, with conventional techniques, the best crystals begin to redissolve because of fluid perturbations at the crystal surface, temperature shifts and other changes in the mother liquor surrounding the crystal. Carrier fluids used to wash the crystal free from the mother liquor or used during mounting of the crystal (for x-ray diffraction) also tend to cause redissolution of the crystal before it can be analysed.

There are many existing methods aimed at enhancing protein crystal growth, some of which take advantage of the favorable crystal growing conditions found in microgravity. An apparatus for carrying out crystallization of proteins and chemical syntheses by liquid-liquid diffusion in microgravity is described in U.S. Pat. No. 4,909,933 (issued to Carter et al.) Another apparatus, disclosed in U.S. Pat. No. 5,130,105 (issued to Carter et al.) relies on vapor diffusion growth of protein crystals. Other recent microgravity-dependent methods are disclosed in U.S. Pat. No. 5,106,592 (issued to Stapelmann et al.), which deal with hanging drop vapor diffusion, dialysis of the protein solution, and interface diffusion between the protein solution and a precipitating agent.

A ground-based (i.e., Earth normal gravity) method of concentrating protein solutions to obtain crystal growth is described by Todd et al. ((1990) *J. Crystal Growth* 110: 283–292), and U.S. Pat. No. 5,104,478 (issued to S. K. Sikdar et al.), which relies on osmotic dewatering of protein solutions. Todd et al. and Sikdar et al. describe the use of a dual chamber device wherein a near-saturated protein solution is separated from a highly osmotic solution by a reverse osmosis membrane which allows dewatering, resulting in supersaturated conditions which in turn cause nucleation and protein crystal growth in the mother liquor. The main advantage of this method is that the rate of dewatering can be determined by the difference in osmotic pressure on either side of the membrane. One drawback of this method is that the nucleation and subsequent protein crystal growth depends on increasing the concentration of precipitant and protein in the mother liquor. There is no control over the effects of solute driven convection on the surface of the crystal. As is the case with the protein crystals grown under conditions of microgravity, the crystals are not protected by any enclosure thus they are subject to physical damage as they are harvested and mounted. None of the existing methods for growing large, perfect crystals provide adequately protected protein crystals.

In conventional x-ray diffraction studies to elucidate the three-dimensional structure of a protein, in order to avoid physical damage to protein crystals, the crystals have typically been mounted in aqueous gels. There are problems, however, in removing the gel material without affecting the integrity of the protein crystal. It would be desirable if a protein crystal could be encapsulated in a shell or membrane that was able to protect the crystal from harsh environments which can cause degradation. A crystal contained within a closed, non-degrading environment would be useful to those working in fields requiring high quality, intact protein crystals. Also needed is a way to grow larger and better quality protein crystals by eliminating some of the physical factors which perturb crystal growth and by better controlling the dewatering conditions to promote single crystal growth. It would be desirable to have a method of preparing protein crystals entrapped in liquid filled microcapsules surrounded by a thin, flexible outer membrane, yet are sturdy enough to protect the enclosed crystals from conditions which might cause fracture or fluid convection that can alter the molecular arrangement at the crystal surface, or dissolution.

Also needed are better carriers for drugs, particularly crystalline drugs, which can resist prematurely rupturing and can provide sustained and/or controlled release at a therapeutic target site, and protect tissues from the sharp edges of the crystals.

SUMMARY OF THE INVENTION

Accordingly, it is an object of the present invention to provide microcapsules containing solutions and/or crystals of bioactive substances such as drugs and proteins, that have semi-permeable membranes which are rugged enough to protect fragile crystals and to resist shear and other mechanical forces typically associated with handling of such crystals.

It is another object of the present invention to provide microcapsules containing highly ordered structures of other bioactive agents, or biomolecules, such as DNA, RNA or oligonucleotides, which are capable of being transported intact through the human vascular system for release at a desired site of action.

It is another object of the invention to provide microcapsules having outer "skins" or membranes which avoid being readily detected and eliminated by the reticuloendothelial system, and which protect the microcapsules against shear forces encountered during use, particularly during transport within the vascular system en route to target tissues.

Another object is to optimize the concentration of a bioactive agent in a microcapsule in order to achieve subsequent sustained or controlled release of the agent.

It is a further object of the invention to provide microcapsules which provide a closed environment that is favorable for growth of crystals under prescribed conditions of dewatering.

Still another object of the invention disclosed herein is to provide a method for making custom microcapsules containing protein crystals of suitable quality for X-ray diffraction studies of native and activated protein structures.

A further object of the invention to provide larger microcapsular packages containing saturated or near-saturated solutions of these bioactive substances than has been possible before, and to provide an environment for these microcapsules that is conducive to growing large crystals inside the microcapsule, or to accommodate larger 3-D ordered structures than has previously been possible.

By entrapping protein crystals in these special purpose microcapsules, they can be protected from conditions which might cause fracture of the crystals or fluid convection which can alter the molecular arrangement at the crystal surface, or dissolution. The semi-permeable membrane provided by the invention not only protects the crystals from harsh environments which can cause degradation, it also provides a closed environment which favors crystal growth under prescribed conditions of controlled dewatering.

In addition to crystallizable proteins or drug that are chemical compounds, many other bioactive substances which are capable of forming a highly ordered structure may be similarly microencapsulated. For instance, a duplex DNA strand or RNA-like structure, or a concentrated solution of an oligonucleotide or a polyribo- or -deoxyribonucleotide or other labile biological are also suitable for entrapment according to the methods of the present invention.

Accordingly, the present invention provides a basic method of making a microcapsule comprising preparing a first phase containing a first solvent, a co-solvent and a first polymer dissolved therein. The method includes preparing a second phase of different density than the first phase, the second phase also including a second solvent, a surfactant, a salt, and a bioactive substance, all dissolved in the second phase. In this method the first polymer and surfactant are selected such that the hydrophobic/lipophilic balance value (HLB) of the surfactant is greater than the HLB of the first polymer. Thusly made, the first and second phases are capable of forming a mutual interface.

The basic method of making a microcapsule that contains a protein or bioactive agent preferably also has a second polymer dissolved in the second phase. In this case, the first polymer, second polymer and surfactant are each selected such that their respective hydrophobic/lipophilic balance values (HLB) are in the following order: surfactant>second polymer>first polymer. Upon bringing the two phases together gently, to form an interface, and by limiting fluid shear forces at the interface to about 0–50 dynes/cm$^2$, microcapsules containing the dissolved bioactive agent are formed. Preferably the shear forces are limited to about 0–100 dynes/cm$^2$ so as to form larger microcapsules.

In preferred embodiments of the invention, the bioactive substance is a protein which is dissolved in the second phase at a concentration that is at or near saturation. In some embodiments, a crystal of the protein is also suspended in the second phase solution. If the protein is particularly susceptible to degradation, a protein stabilizing agent may be included in the second phase solution.

The first solvent is preferably water, methanol, ethanol, isopropanol, n-hexanol, or n-heptanol, or a hydrocarbon having a low or medium HLB 5–10. The co-solvent is preferably a 3-carbon to 8-carbon ($C_3$–$C_8$) normal alcohol, tetrahydrofuran, dioxane, acetonitrile, dimethylformamide, dimethylacetamide, dimethylsulfoxide or a similar solvent.

The first polymer is preferably a polymer of glycerol monostearate, glycerol monooleate, glycerol monolaurate, glycerol dioleate, glycerol distearate or other hydrophobic mono- or polyglycerides or waxy polymers of low molecular weight, or it can be a combination of any of those polymers. In an alternative method of the invention, however, the first solvent is water and the first polymer is a polyethylene glycol having a molecular weight greater than about 400 kd, cyclodextrin, polyvinylpyrrolidine or polyvinyl alcohol. In another alternative embodiment, an alternative membrane forming material comprising a sterol or a phospholipid is substituted for the first polymer. The sterol or phospholipid may be cholesterol, stigmasterol, phytosterol, campesterol, phosphatydyl choline or CENTROLEX-F™.

In preferred methods of making the microcapsules of the present invention, the second solvent is water and the surfactant has a hydrophilic/lipophilic balance value (HLB) of about 10–40. The HLB of the first polymer is preferably less than the HLB of the surfactant by 2 or more HLB units. The surfactant may be chosen from the group consisting of sorbitan monooleate plus ethylene oxide, dextran, polyethylene glycol (PEG), $C_{12}$–$C_{20}$ fatty acids, and quaternary $NH_4$ salts.

The second polymer is preferably capable of adhering to the first polymer and is chosen from the group consisting of PEG 400–20000, dextran 4000–20,000, a polysaccharide of mol. wt. ranging from about 10,000–100,000, polyvinylpyrrolidone (PVP), a polyvinyl alcohol and other similar polymeric materials.

In preferred embodiments the salt contained in the second phase solution is NaCl, KCl, $CaCl_2$, quaternary $NH_4$ salts, cetyl trimethylammonium bromide, 2-amino-2-methyl aminomethyl propanol or a similar salt.

According to the preferred methods of the invention, after initial formation of the microcapsule, the membrane is allowed to cure. After curing, the relatively sturdy microcapsules may be separated into fractions of a certain size range, if desired for a particular purpose, such as injection into a blood vessel for therapeutic treatment. After curing, the microcapsules may then be subjected to gradual dewatering in order to gently bring about supersaturation of the bioactive agent and to encourage single crystal nucleation and growth. Optionally, an additional coating of polymer may be applied to the microcapsule, after curing, after dewatering, or after full growth of the crystal has been accomplished, in order to provide a thicker, more protective skin on the microcapsule.

The dewatering step of certain embodiments of the invention may include exposing the microcapsule to a closed local environment which is capable of regulating the rate and extent of microcapsule dewatering whereby controlled crystallization of a protein occurs within said microcapsule. The dewatering step may include exposing microcapsules to a dewatering solution containing a salt or a polymer which is excluded by the semi-permeable membrane of the microcapsule. In an alternative embodiment, the method includes diffusing a low molecular weight salt into said interior cavity to induce single crystal nucleation and crystal growth.

In certain embodiments employing a closed local environment for dewatering the microcapsule, the environment may also permit controlling the protein concentration and the concentration of charged precipitant molecules at or near the surface of a growing protein crystal so that the internal order and extent of crystallization of said protein crystal is optimized.

One preferred method of making a microcapsule includes preparing a first phase containing a first solvent chosen from the group consisting of: methanol, ethanol, isopropanol, m-hexanol, or n-heptanol, a co-solvent chosen from the group consisting of: a 3-carbon to 8-carbon ($C_3$–$C_8$) normal alcohol, and a first polymer dissolved in the first phase. The first polymer is a hydrophobic mono- or polyglyceride. According to this method, a second phase is also prepared, the second phase having a different density than that of the first phase. The second phase is water containing polyethylene glycol, as a surfactant, and a second polymer dissolved therein. This second polymer, which is capable of adhering to the first polymer, is PEG 1000–8000. A protein is also dissolved to saturation or near-saturation in the second phase. Optionally, one or more crystals may also be suspended in the second phase solution. The second phase also includes NaCl dissolved therein. An important feature of this method is that the first polymer, second polymer and surfactant are chosen such that the hydrophobic/lipophilic balance values (HLB) are: surfactant>second polymer>first polymer. When the two phases are gently brought into direct contact, an interface forms between them. It is a critical part of this method that the fluid shear stress at the interface be limited to 0–100 dynes/$cm^2$ so that microcapsules having the desired characteristics will form. After microcapsules have formed, the outer membrane is then cured to make it more rugged and durable. Optionally, an additional polymer coating may be applied over the outer membrane if an even thicker membrane, or skin, is desired.

Also provided in accordance with the present invention is an improved method of determining the three-dimensional structure of a predetermined protein molecule by x-ray crystallography. The improvement includes forming a microcapsule containing a saturated or near saturated aqueous solution of a protein surrounded by a semi-permeable polymeric membrane. The microcapsule is exposed to a dewatering solution having a higher osmotic pressure than the encapsulated protein solution, whereby water is osmotically removed from said encapsulated protein solution. By controlling the concentration of a dewatering agent in the dewatering solution, gradual, ordered crystallization of the protein occurs within the microcapsule. This gradual, ordered crystal growth is allowed to continue until the crystal becomes at least about 50–300 microns across one face. A microcapsule containing a crystal of sufficient size and crystalline quality is then carefully selected. The microcapsule is mounted in an x-ray capillary tube and subjected to a high energy x-ray crystallographic procedure to obtain a characteristic x-ray diffraction pattern of the protein crystal.

In an alternative and preferred method of performing x-ray crystallography on a crystal specimen, the present invention provides an improvement over methods which include isolating a crystal specimen in a fiber loop with an attached handle portion, freezing the crystal specimen, mounting the crystal specimen and fiber loop on a goniometer head such that said crystal is positioned in a continuous $N_2$ stream loop, and rotating the goniometer head in an x-ray beam. The present improvement includes substituting for the conventional crystal specimen a microencapsulated crystal that has a protective outer membrane surrounding a large crystal and a small amount of mother liquor. The membrane, which is preferably a composite of two or more polymers, is substantially transparent to the x-ray beam so that it does not interfere with the x-ray diffraction pattern of the crystal. According to this improved method, the membrane has an electrostatic charge which renders the microencapsulated crystal electrostatically attracted to the fiber loop. This electrostatic attraction is strong enough to support the microencapsulated crystal inside said loop. Optionally, a drop of liquid may be adhered to the outer membrane of the microencapsulated crystal to facilitate freezing. In certain embodiments the membrane is negatively charged and the loop is a fiber having a positive electrostatic charge. In certain preferred embodiments the crystal is a highly ordered protein crystal.

The present invention also provides a microencapsulated protein crystal prepared by certain methods described above. In some embodiments the microcapsule is best characterized as a product of a particular method of the invention, because the inventors believe that there are as yet unrealized features and characteristics of the new microcapsules which are attributable to the novel method of making.

In accordance with the present invention, a microcapsule is provided having an outer membrane surrounding an interior cavity, the interior cavity containing a saturated or nearly saturated solution of a bioactive agent. An important feature of this new microcapsule is that it is capable of withstanding shear forces at least as great as the turbulent blood flow within a human artery.

Certain embodiments of the new microcapsule have a membrane containing at least one of the membrane forming material materials described above in the summary of the methods, descriptions. In the preferred embodiments, the membrane is a composite containing a first polymer and a second polymer that is capable of adhering to the first polymer. The HLB of the second polymer is preferably greater than the HLB of the first polymer.

In certain embodiments of the microcapsule of the present invention, the interior cavity also contains the protein or bioactive agent in the form of a highly ordered structure such as a crystal. In some embodiments the crystal substantially fills the interior cavity. The membrane may even substantially conform to the shape of a large crystal. In preferred embodiments, the membrane is resistant to rupturing or piercing by the crystal.

In certain embodiments the microcapsule's membrane is permeable to water and low molecular weight salts but impermeable, or only slightly permeable, to the bioactive agent. In some embodiments, the membrane is less than or equal to 1 micron in thickness, and in others the membrane is about 3–5 microns thick.

Preferably the bioactive agent is a protein or a drug, however in some embodiments of the microcapsule of the invention the bioactive agent is a biomolecule such as a polypeptide, oligonucleotide, RNA, DNA or other compound which can be crystallized.

Certain embodiments of the new microcapsule include a highly ordered structure, such as a crystal, about 50–2000 microns in size.

Certain alternative embodiments of the microcapsule of the invention have an interior cavity that contains a hydrophobic phase surrounded by and partially immiscible with a saturated or near-saturated solution of the bioactive agent.

Also provided by the present invention is a composition comprising a multiplicity of certain microcapsule of the invention suspended in an aqueous solution having higher osmotic pressure than that of the bioactive agent solution. The higher osmotic aqueous solution may include a dewatering agent capable of causing water to be transported through said membrane and out of said interior cavity. This dewatering agent may be a salt or a high molecular weight polymer which is excluded by said membrane.

Certain embodiments of the new microcapsules have a polymeric membrane that is transparent to x-ray radiation and/or does not interfere with the x-ray diffraction pattern of the highly ordered structure.

The present invention accordingly provides an x-ray crystallography reagent for use in elucidating the three-dimensional structure of a predetermined biomolecule which is capable of forming a highly ordered structure. The reagent comprises a dewatered microcapsule prepared according to certain methods of the invention and having a highly ordered structure, such as a protein crystal, substantially filling the interior cavity of the microcapsule.

The present invention also provides a pharmaceutical composition comprising a pharmacologically effective multiplicity of certain microcapsules of the invention, together with a pharmacologically acceptable carrier. For particular medical uses, the average size of the microcapsules is about 1–20 microns, and for others the average size of said microcapsules is about 50–300 microns, or even greater than about 300 microns.

BRIEF DESCRIPTION OF THE DRAWINGS

FIG. 3 show concanavalin A inside microcapsules of the present invention.

FIG. 6 shows cis-platin crystals inside microcapsules of the present invention.

FIG. 6C is similar to FIG. 6A but includes superimposed fitted lines for measurement of crystal size.

DETAILED DESCRIPTION OF PREFERRED EMBODIMENTS

Figure 1A:
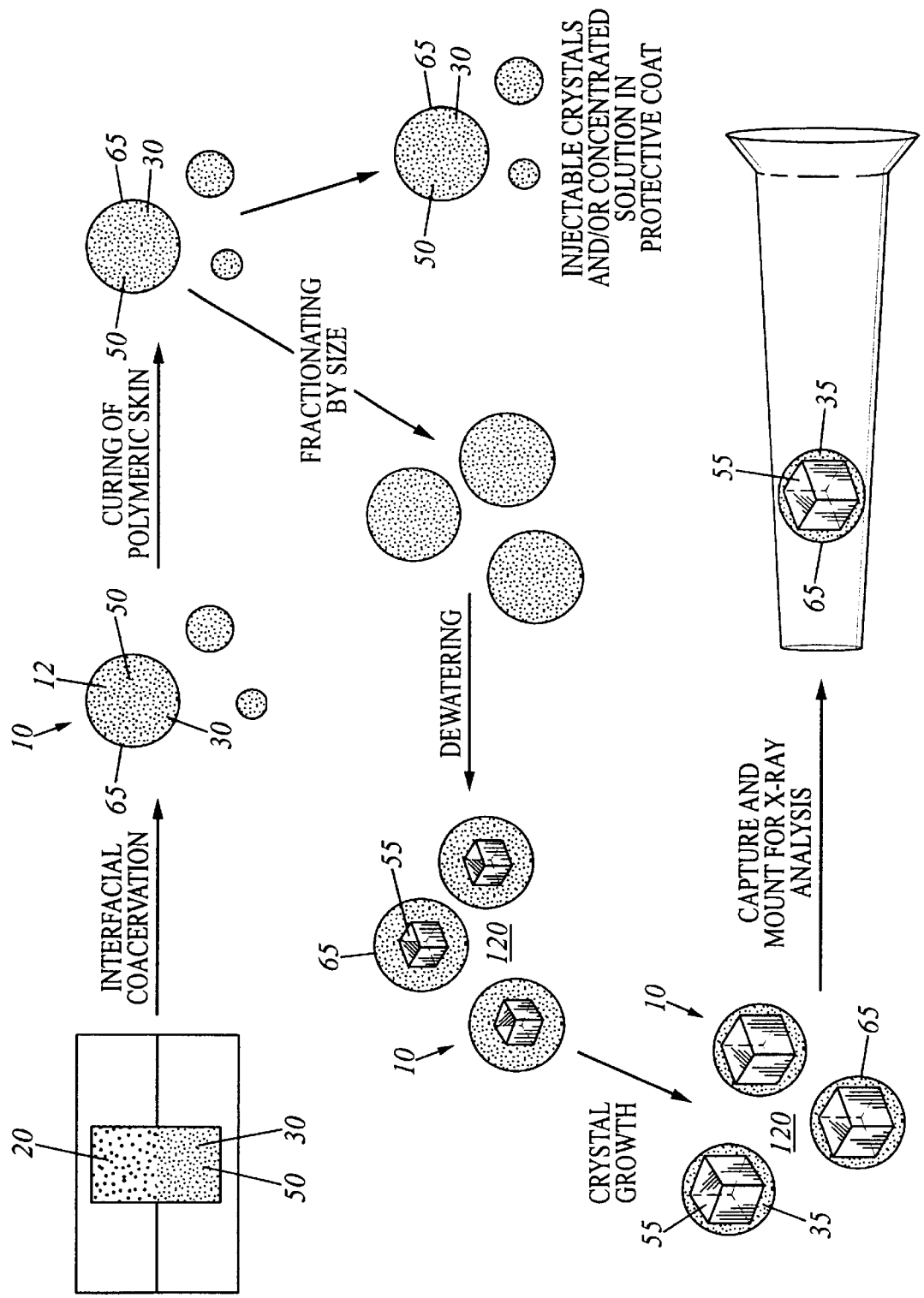
FIG. 1A is a conceptual diagram of the procedure for forming a microcapsule of the present invention and for obtaining crystal growth within the microcapsule and mounting the encapsulated crystal for x-ray diffraction analysis.

Microgravity research has provided a new understanding of mechanisms of fluid mechanics, interfacial behavior, and many biological processing methods that are compromised by gravity-dependent phenomena. As demonstrated by the inventors in U.S. patent application Ser. No. 08/349,169 (now U.S. Pat. No. 5,827,531), liquid microcapsules having two or more concentric layers can be made in a single step by slowly bringing two immiscible liquid phases (of differing densities) together under conditions where the surface tension and diffusive forces are greater than the convective forces. The mechanisms of spontaneous formation of large microcapsules in microgravity have been further investigated by the inventors to develop new methods to make these and other unique microcapsules in both Earth-based and in microgravity environments. The disclosure of U.S. patent application Ser. No. 08/349,169 (now U.S. Pat. No. 5,827,531) is incorporated herein by reference.

There are no prior art methods wherein protein crystals are encapsulated in a semi-permeable membrane which protects the crystals from harsh environments which can cause degradation. For the purposes of the present disclosure, the term "semi-permeable membrane" includes the usual definition and, when the context allows, also means that water and low-molecular weight salts can pass through the membrane, but the membrane is impermeable to a protein or other bioactive agent contained by the microcapsule of the present invention.

Neither are there any prior art methods that provide a closed environment that favors crystal growth under prescribed conditions of controlled dewatering within a microcapsule or inside a polymer membrane. Known methods utilizing osmotic dewatering for growing protein crystals has relied on use of small chambers having a planar reverse osmosis membrane positioned between the mother liquor and the dewatering (high osmotic pressure) salt solution. The present method uses spherical microcapsules wherein the entire outer membrane surface is available for osmotic dewatering, also for infiltration by hydrogen or hydroxyl ions thereby changing the pH within the microcapsule to favor or enhance protein saturation and subsequent crystal growth. The membrane also can allow diffusion of salt ions into the microcapsule to decrease the solubility of the protein or bioactive agent. The increased surface area of the spherical microcapsule allows for more rapid change in conditions throughout the sphere of mother liquor, hence faster controlled changes all around the crystals which enhances the formation of more ordered and perfectly formed crystals.

EXAMPLE 1

General Procedure for Microcapsule Preparation

Gravity-dependent restrictions in the basic liquid-liquid spontaneous microencapsulation process led to the design of several microgravity experiments to explore the utility of this process when density-driven phenomena were eliminated. In particular, density-driven, gravity-dependent restrictions of the liquid-liquid microencapsulation process were: early phase separation producing fragile microcapsules; and interfacial dynamic flow causing coalescence of microcapsules. Failure of early ground-based experiments to derive uniform microcapsules lead to a desire to attempt microcapsule formation in space.

The microgravity flight experiments led to the development of a liquid-liquid microencapsulation process that involves use of surfactants and co-surfactants in the aqueous phase and co-solvent/co-surfactant alcohols in the organic phase, which also contained high molecular weight polymers that formed a tough, yet flexible, outer "skin" on the final microcapsules. The inventors' earlier work in microgravity conditions included a single step dispersion which produced unique multi-lamellar microcapsules containing various aqueous drugs co-encapsulated with iodinated poppy seed oil (a radiocontrast medium with a sp. gravity= 1.35). Subsequent ground control experiments also produced some of these unique microcapsules and illustrated that the Earth normal (1 g) process could be improved to yield useable microcapsules by varying the liquid phase formulations.

In further studies, it has become clear that the flexible outer skins, or membranes substantially improve the ruggedness of the microcapsules formed. The inventors have gone on to develop a method of forming microcapsules that have a low molecular weight, water permeable outer "skin" or membrane surrounding a sphere of aqueous mother liquor containing a dissolved protein. The method utilizes a protein-impermeable polymer dissolved in a liquid organic phase. Formation of the microcapsule occurs by interfacial coacervation at the immiscible interface of the organic and aqueous phases, trapping the protein "mother liquor" inside.

The general procedure for forming microcapsules is essentially as disclosed by the inventors in U.S. Pat. No. 5,827,531, and as described below. The disclosure of that application is incorporated herein by reference, to the extent that it provides details supplementary to those set forth herein.

The method of the present invention relies on liquid-liquid interactions. In the basic method, the first step entails formulating a first phase or layer ("Phase 1") while the second step entails formulating a second phase or layer ("Phase 2"). The two phases are formulated to be substantially immiscible with one another. For the purposes of this invention, "immiscible" means that the two adjoining phases or layers have sufficiently different densities, viscosities or surface tensions to permit the formation of a mutual interface resembling a meniscus, or visible interface.

As shown in Table 2 and the details that follow, formulating Phase 1 comprises combining a first solvent (which is preferably hydrocarbon based), a first polymer soluble in the first phase and a co-solvent. The first polymer is selected to be one which is soluble in the first phase and when formed into the microcapsule membrane is permeable to aqueous solvents and ions but impermeable to proteins or peptides. A small amount of a co-solvent is also added to the first phase, which co-solvent may also function as a co-surfactant.

The method next calls for formulating a second phase ("Phase 2"), which is preferably aqueous and is immiscible with the first phase. The second phase comprises a second solvent, a second polymer soluble in the second phase but insoluble in the first phase, a surface active agent ("surfactant"), a dissolved salt and a dissolved protein or other bioactive substance of interest. The bioactive substance may also be in the form preformed crystals suspended in a concentrated solution of the same bioactive substance.

In order to ensure that the liquid-liquid interactions necessary to form the microcapsule will occur, certain of the constituents of Phases 1 and 2 are selected relative to one another (i.e., based on certain characteristics of one component, the second is selected advantageously based on its respective characteristics. After selecting the immiscible organic and aqueous solvents, the surface active agent in the second phase is selected such that it will have a hydrophilic/ lipophilic balance ("HLB") value greater than that of the first polymer constituent of the first phase (Polymer 1).

Generally, the most useful surface active agents are those which are nonionic and which have a hydrophilic/lipophilic balance value of 10.0 or greater. Next, the second polymer constituent of the second phase (Polymer 2) is selected to have a hydrophilic/lipophilic balance value lower than that of the surface active agent constituent of the same phase. While not an exhaustive list, certain hydrophilic/lipophilic balance values of materials which may be used in the formulations of the invention as Polymer 1 or Polymer 2 are provided in Table 1 below. See McCutcheon's Detergents and Emulsifiers (1979) North American Edition, McCutcheon Division, MC Publishing Co., 175 Rock Road, Glen Rock, N.J. 07452, for specific HLB values ranging from 2 to 42, see pages 23–39; and for HLB values ranging from 0.5 to 30.5, see pages 228–241. In making suitable polymer selections, it is important that the first polymer have an HLB value less than that of the surface active agent which, in turn, has an HLB value which is greater than that of the second polymer.

TABLE 1

HYDROPHILIC/LIPOPHILIC BALANCE (HLB) (McCutcheon 1979)

| Compound | HLB |
| --- | --- |
| Glycerol treioleate | 0.8 |
| Cholesterol | 1.0 |
| Triglyceride of coconut oil | 1.4 |
| Sorbitan trioleate | 1.8 |
| Sorbitan tristearate | 2.1 |
| Glycerol monooleate | 2.7 |
| Mono and di glycerides of fat-burning fatty acids | 2.8 |
| Glycerol Monostearate (gms) | 2.8–5.0 (3.8 preferred) |
| Propoxylated ethylene diamine plus ethylene oxide | 3–28 |
| Mono/diglyceride | 3.2 |
| Glycerol mono coconut | 3.4 |
| Mono/diglyceride | 3.5 |
| Propylene glycol mono fatty acid ester | 3.5 |
| Monoethoxyl lauryl ether | 3.6 |
| Stearyl lactyl acid | 3.8 |
| Hydrogenated cottonseed oil | 3.8 |
| Sodium lauryl sulfate | 4.0 |
| Mono and diglycerides with citric acid or lactylic ester or fatty acid | 4.2–4.6 |
| Ethoxylated fatty amine (2 moles ETO) | 4.5 |
| Diethylene glycol monostearate | 4.7 |
| Sorbitan monopalmitate | 4.7 |
| Diethylene glycol monostearate and oleate | 4.7 |
| Ethoxylated (2) cetyl ether | 5.3 |
| Glycerol Monoricinoleate | 6.4 |
| Glycerol monolaurate | 6.8 |
| Triglycerol mono stearate | 7.0 |
| Polyethylene glycol (400 dioleate) | 7.2 |
| Lanolin sterol | 8.0 |
| Ethoxylated nonyl phenol (CO-420 & CO 850) | 8.0–16.0 |
| Polyethylene glycol (400) distearate | 8.2 |
| Sorbitan monolaurate | 8.6 |
| Ethoxylated sorbitan fatty acid esters and alkyl/aryl alcohol | 9.0 |
| Anhydrous lanolin | 10.0 |
| Polyethylene glycol monostearate | 11.0 |
| Polyethylene glycol 400 | 11.2 |
| Ethoxylated (10) cetyl ether | 12.9 |
| Ethoxylated glycerol monostearate (GMS) | 13.1 |
| Sorbitan monostearate | 14.9 |
| Sorbitan monooleate with 20 moles ethylene oxide | 15.0 |
| Ethoxylated (20) oleyl ether | 15.3 |
| Ethoxylated (20) stearyl cetyl ether | 15.8 |
| Ethoxylated castor oil | 18.0 |
| Nonyl phenol polyethylene glycol ether | 18.1 |
| Polyethylene glycol 600 mono laurate | 19.6 |
| Sodium lauryl sulfate | 40 |
| Propylene glycol monostearate | 40 |
| Hydroxylated lanolin sodium oleyl sulfate | 42 |

TABLE 1-continued

HYDROPHILIC/LIPOPHILIC BALANCE (HLB) (McCutcheon 1979)

| Compound | HLB |
| --- | --- |
| Blends of GMS and sorbitan monooleate with 20 mols ethylene oxide | 52 |

TABLE 2

General Formulations for the Two Phases

| Phase 1 | | Phase 2 | |
| --- | --- | --- | --- |
| 75–90% (v/v) | Solvent 1 | 70–98% (v/v) | Water |
| 0–20% (v/v) | Co-solvent | 1–4% (w/v) | Surfactant |
| 1–5% (w/v) | Polymer 1 | 1–10% (w/v) | Polymer 2 |
| | | 1–3% (w/v) | Salt |
| | | 1% to saturation | Bioactive Substance |

Solvent 1

Solvent 1 is preferably ethanol, methanol, isopropanol, n-hexanol, or n-heptanol, or another hydrocarbon having a low or medium HLB of 5–10. As a less preferred alternative, water may be substituted for the hydrocarbon if, for example, it is desirable to avoid the use of a hydrocarbon.

Co-Solvent

The Co-solvent is a 3-carbon to 8-carbon ($C_3$–$C_8$) normal alcohol, tetrahydrofuran, dioxane, acetonitrile, dimethylformamide, dimethylacetamide, dimethylsulfoxide or the like. An acceptable co-solvent also acts as a surfactant and preferably has a high dielectric constant, i.e. in the range of about 10–20.

Polymer 1

Suitable outer skin forming compounds which can be used as Polymer 1 are: glycerol monostearate, glycerol monooleate, glycerol monolaurate, glycerol dioleate, glycerol distearate, or other hydrophobic mono- or polyglycerides or waxy polymers of low molecular weight, or a combination of the foregoing polymers, which are capable of forming a thin, semi-permeable membrane.

Alternatively, a hydrophobic aqueous phase may be substituted for the Phase 1 liquid, if desired, as mentioned above with respect to Solvent 1. In this alternative water is used as the primary solvent and a polymer such as a high molecular weight polyethylene glycol (mol. wt. greater than 400 kd), cyclodextrin, polyvinylpyrrolidine or polyvinyl alcohol is dissolved therein. The particular polymer selected should be insoluble in the second aqueous phase (Phase 2).

It was somewhat surprising to the inventors that other chemicals not strictly considered polymers, such as lecithins, when used to make the microcapsules of the invention, also laid down a polymer-like skin or film at the interfaces of the two phases. Thus, depending on the characteristics of the particular bioactive agent selected for encapsulation, the following sterols and phospholipids may be substituted for Polymer 1: cholesterol, the plant sterols stigmasterol, phytosterol and campesterol, or lecithins such as phosphatydyl choline (CENTROLEX-F™). In any event, acceptable hydrocarbon-soluble polymers (or non-polymeric membrane forming materials which can substitute for Polymer 1), will generally have lower HLB values, in the order of less than 1 to about 12. Polymer 1 is insoluble or sparingly soluble in water.

Polymer 2

Polymer 2 is water soluble and is preferably chosen from the following: PEG 400–20000, dextran 4000–20,000, a polysaccharide of mol. wt. ranging from about 4,000–100,000, polyvinylpyrrolidone (PVP), a polyvinyl alcohols or another similar polymeric material. Polymer 1 and Polymer 2 are selected such that they cannot solubilize each other, and they do not chemically react to form new and distinct adducts. Preferably Polymer 2 is capable of adhering to Polymer 1, however, and in preferred formulations the microcapsule's final, or "cured," membrane is actually a composite of Polymers 1 and 2. In this case, Polymer 2 serves to enhance the strength of the outer membrane or skin, which is primarily made up of Polymer 1. It should be noted that the inventors have succeeded in making protein- and crystal-filled microcapsules using only Polymer 1 as the skin-forming material. However, a sturdier membrane is obtained when the second polymer, Polymer 2, is included. Using the same rationale for selection, additional suitable polymers could be included in the Phase 1 of Phase 2 solutions to form the composite polymeric skin.

Surfactant

A suitable surfactant for dissolving in the aqueous Phase 2 solution can be any of the following ionic or non-ionic compounds: sorbitan monooleate plus ethylene oxide, dextran, polyethylene glycol (PEG), $C_{12}$–$C_{20}$ fatty acids or a quaternary $NH_4$ salt. The surfactant chosen will typically have a higher HLB value, in the range of about 10 to 40. The surface active agent is selected so that it has an HLB value sufficiently different (preferably HLB>2 or more units different) from that of either polymer 1 or 2, so that the surfactant will lower the interfacial tension just enough to promote film (outer skin) formation by polymer 1 and/or polymer 1 plus polymer 2. but does not lower the surface tension enough to cause complete emulsification of the skin polymer(s) in the second solvent. The surfactant itself does not form a major component of the outer film, or skin, which surrounds the microcapsule, encapsulating the drug or other bioactive agent.

Salt

Suitable salts are NaCl, KCl, $CaCl_2$, quaternary $NH_4$ salts, cetyl trimethylammonium bromide, 2-methyl-2amino-aminomethyl propanol or another similar salt.

Bioactive Substance

The protein or bioactive substance, or agent, is preferably a protein that can be crystallized, but it may also be another bioactive substance or agent that is compatible with the microcapsule-forming materials and is capable of forming a crystal or other highly ordered structure. Some other types of molecules that are suitable for encapsulating are structures such as a double stranded DNA α-helix, polypeptides, oligonucleotides, D- or L-stereoisomers, pharmaceutical compounds, toxic agents, and the like. A protein stabilizing agent may also be included in the Phase 2 solution when the substance to be microencapsulated is a protein that is easily degraded. Some suitable protein stabilizing agents are benzamidine and 2-MP.

Optionally, an oil can be added to the Phase 1 solution. For example, in some applications it may be desirable to include a marker or tracer for tracking the location of the microcapsule in the body. A radiocontrast material such as iodinated poppy seed oil (IPO) could be incorporated into the microcapsule to permit detection by radiographic techniques.

The preceding formulations have been used successfully by the inventors in both Earth normal and in microgravity environments to form liquid-filled microcapsules.

The basic method next creates an interface between the first and second phases. The creation of the interface is achieved in such a way that minimal shear and mixing occurs between the phases. The two immiscible phases are brought together in such a mechanical manner that the fluid shear properties are controlled to low levels from 0 to 100 dynes/cm$^2$, preferably below 50 dynes/cm$^2$, and most preferably 12 dynes/cm$^2$ or below, such that the adsorptive surface properties at the immiscible interfaces are not significantly altered. Although the exact mechanisms are not fully understood, the inventors believe that the maintenance of certain adsorptive surface properties, such as the surface tension, Helmholtz charge distribution (electrical double layer), and partitioning of the surfactant molecules between the immiscible phases must remain substantially intact so that lateral phase separation of phases can occur to form the water/organic interface. This is believed to be the mechanism for the formation of multi-lamellar vesicles which are formed in a single step, as discussed in U.S. patent application Ser. No. 08/349,169 (now U.S. Pat. No. 5,827,531). Although best demonstrated under microgravity conditions, wherein buoyant convection is absent and diffusion-driven convection predominates, favorable microcapsule forming conditions are also accomplished in unit gravity environment by balancing the density differences between the two liquid phases or by any other mechanical means which prevents excess fluid shear from significantly altering the normal adsorptive surface properties which are determined by the chemical composition of the formulas and the interfacial phenomena among the solvents, polymers and surfactants, as described above. One way of creating a suitable interface is by sliding individually separated compartments containing the two phases into register with one another in a manner that substantially limits shear and provides gentle mixing, as shown in the schematic illustration in FIG. 1A.

Interface Formation

Figure 3A:
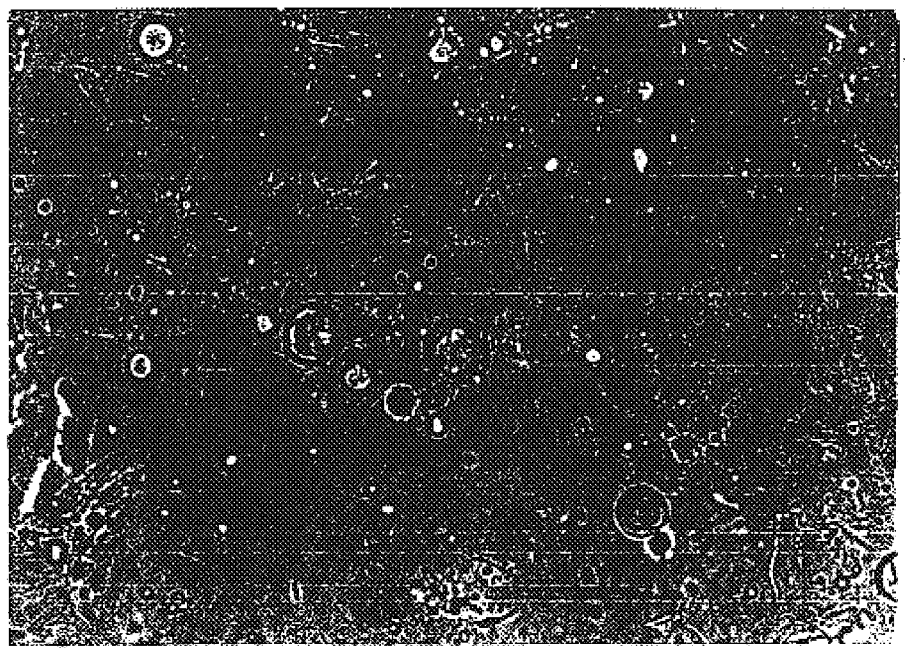
FIG. 3A is a photomicrograph showing concanavalin A crystals and solution contained in a microcapsule of the present invention formed at 1 g (magnification=150×).
Figure 3B:
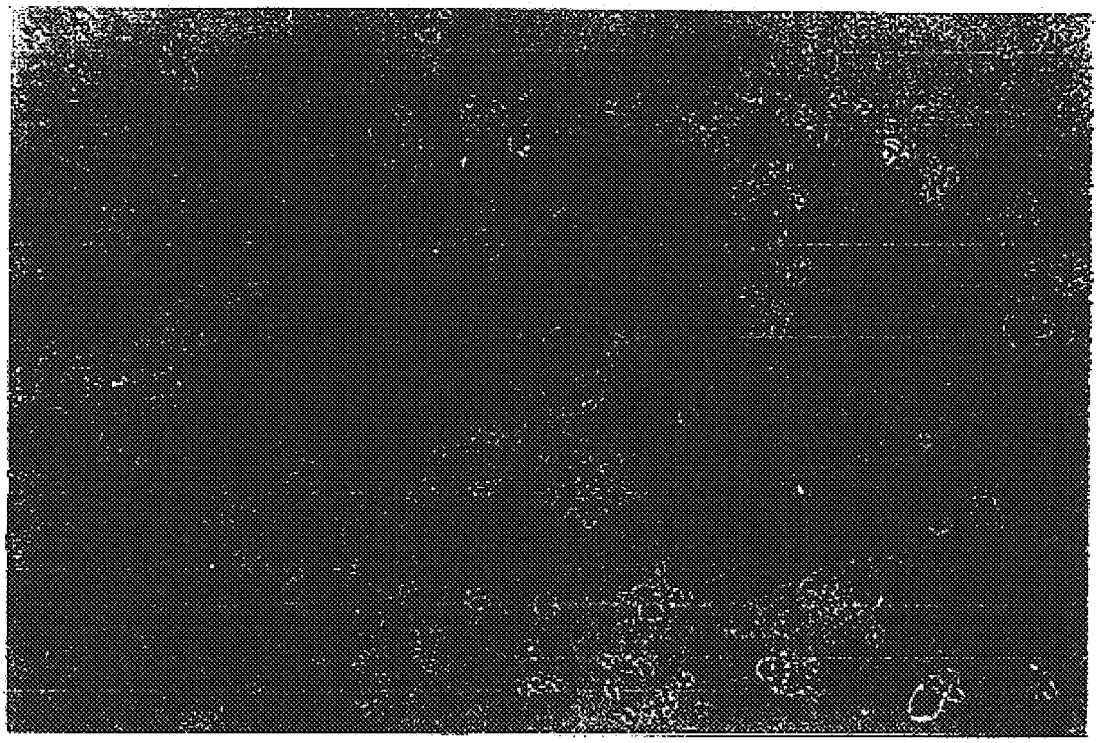
FIG. 3B is a photomicrograph showing concanavalin A crystals and solution contained in a microcapsule of the present invention formed in microgravity conditions aboard the Space Shuttle (magnification=150×).

The two liquid phases formulated as described above are placed into separate compartments or spaces which are each connected to a central diffusion chamber into which each compartment can deliver its resident liquid loading. The compartments are initially closed to access into the central diffusion chamber so that the first and second liquids are kept apart from one another and not allowed to interact. The separation of the two liquids is maintained until both liquids and the device containing them can be placed in an environment in which convective mixing may be minimized, such as in a microgravity environment. FIG. 1A is a schematic illustration of one way that a liquid-liquid interface may be achieved, and shows conceptually the structure of the microcapsules formed. While it is possible to use any number of devices to accomplish this separation, a preferred apparatus for use in creating the optimal low-shear conditions favoring spontaneous interfacial coacervation is the Materials Dispersion Apparatus (MDA) (manufactured by ITA, Inc., Exton, Pa.), which is described in U.S. patent application Ser. No. 08/349,169 (now U.S. Pat. No. 5 827,531). Another suitable apparatus is the Microencapsulation Electrostatic Processing System (MEPS), which is described in a companion U.S. patent application entitled "Microencapsulation and Electrostatic Processing Device" application Ser. No. 09/079,833(NASA No. MSC-22937-1-SB), which application is incorporated in pertinant part herein by reference. Any suitable apparatus capable of slowly and gently bringing two immiscible liquid phases of differing densities together and permitting spontaneous formation of microcapsules may be used however, as long as the required low shear conditions (i.e., 0–100 dynes/cm$^2$) are maintained. Shear forces of 35 dynes/cm$^2$ and below have been demonstrated by the inventors during the spontaneous formation of representative microcapsules at the interface of the two phases under conditions of Earth normal gravity and in microgravity, as illustrated in FIGS. 3A and 3B, for example.

Calculations were made for shear forces occurring in various types of apparatus which have been used to successfully make the multi-layered microcapsules. Original calculations for shear stress in cell syringes were extended to calculations for Liquid Mixing Apparatus (LMAs) made by ITA, Inc. in Exton, Pa. Microcapsules were formed using several representative formulations taken from Table 2, for the alcoholic (Phase 1) and aqueous (Phase 2) phases.

In order to form microcapsules, the interfacial surface tension must not be overcome by shear stresses, at least until the "outer skin" has formed and stabilized, after which the microcapsules can withstand even higher shear stress. The toughened outer skin can be observed by observing a sample of the microcapsule suspension under the microscope. The microcapsules tumble in gentle fluid flow rather than disintegrate. A basic assumption is that the microcapsules do not form efficiently in the high shear stress fields within a distance equal to three (3) diameters from the container walls or immiscible interface. The following calculations indicate that most 10 micron diameter microcapsules would be formed in the boundary layer from 30 microns to 0.2 cm of the immiscible interface.

Shear-Laminar Flow Boundary Layer calculations for forming representative microcapsules including the following assumptions: the two fluids are incompressible, immiscible and one acts similar to a solid wall; the viscosity of Phase 1 (Med-10) at 20° C. ($\mu^1$) is 0.01716 g/cm-sec; the viscosity of Phase 2 (aqueous Cis-Platinum-II) ($\mu^2$) is 0.0101 g/cm-sec; the average dynamic viscosity ($\mu'$) is 0.01363; the density of Phase 1 ($\rho^1$) is 0.802; the density of Phase II ($\rho^2$) is 1.009; the effective kinematic viscosity (v') is 0.015703, where (v')=(($\mu^1/\rho^1$)+($\mu^2/\rho^2$))/2; the maximum fluid velocity along the container wall or immiscible interface=$V_{max}$, i.e., 14.29 cm/sec.

Shear Stress ($\tau$) is $$\tau = \frac{(0.332)(\mu)(V_{max})\sqrt{\frac{V_{max}}{v'}}}{\sqrt{x}}$$

$$\text{where } \mu = \frac{(\mu^1 + \mu^2)}{2}$$

$$\text{and } \tau = \frac{1.949812}{\sqrt{x}}$$

where x=distance (cm) from wall or interface
Therefore, when x=

| μm | cm |
|---|---|
| 30 | 0.003 |
| 50 | 0.005 |
| 100 | 0.010 |
| 200 | 0.020 |
| 300 | 0.030 |
| 500 | 0.050 |
| 600 | 0.060 |
| 900 | 0.090 |
| 1000 | 0.100 | then $\tau$=

| (dynes/cm²) |
|---|
| 35.6 |
| 27.57 |
| 19.50 |
| 13.79 |
| 11.26 |
| 8.72 |
| 7.96 |
| 6.50 |
| 6.17 |

Thus, the fluid shear stress at 30 microns is 35.6 dynes/cm² and is reduced to 11 dynes per cm² at 300 microns from the interface. In each instance, microcapsules were observed to form. Experiments performed in the inventors' laboratory indicate that the microcapsules of most interest (i.e. >10 microns in diameter) do not form within 3–4 diameters (30–50 microns) from the interface. The microcapsules described in these Examples were formed using the basic procedure described above, in shear fields calculated to be approximately 35 dynes/cm². The largest microcapsules (i.e., ranging from about 50 microns to 2 mm), which are especially preferred for crystal x-ray diffraction studies, are probably best formed in the more quiescent region of the boundary layer which is about 100 microns or farther from the container wall. This corresponds to a shear stress field of 19 dynes/cm² or less. When microcapsules of about 20 microns in size are desired, such as for in vivo use as drug carriers, relatively higher shear conditions are permissible.

Minimal shear conditions are critical in gravity dependent conditions (i.e., ≧1 g). In this case, the optimum microcapsules are formed when the fluid shear between the immiscible Phase 1 and Phase 2 liquids is restricted to 10–100 dynes/cm². Under microgravity conditions (i.e., <1 g) the fluid shear forces can be better controlled in the range of about 2–30 dynes/cm².

In the next step of the basic method, conditions are established for substantially limiting all mixing between the interfaced liquid phases. Preferably, the two phases are allowed to interact at their interface without agitation, stirring, shearing or like force for a period of about 1–10 minutes. Preferably the temperature is maintained within about ±1° C. of the maximum solubility temperature of the polymer, but below the denaturation temperature of the protein or other bioactive substance. For representative proteins and drugs demonstrated in these examples, temperatures up to 43° C. are maintained. It is preferred to limit even those quiescent forces such as gravity-controlled sedimenting, shifting, drift and the like. Thus, it is low fluid shear, chiefly diffusion-driven convection, that is used to spontaneously form microcapsules, as the chemical formulations of the different phases assist in lowering the surface free energy across the interface. It is also at this time that formation of the polymeric outer coating is initiated. The inventors' recent investigations indicate that, in either unit gravity or microgravity conditions, it is advantageous, however, that the two phases be allowed to interact at their interface with a small amount of fluid shear force applied (approximately 2–40 dynes/cm$^2$), in order to increase the yield of microcapsules. The maximum practical shear force is a function of the kinematic viscosity of each fluid at the interface. The shear force should not produce a Reynolds number greater than 300. Uniformity and sphericity is a common characteristic of the microcapsules of the invention, regardless of the gravity environment in which they are produced.

Figure 1B:
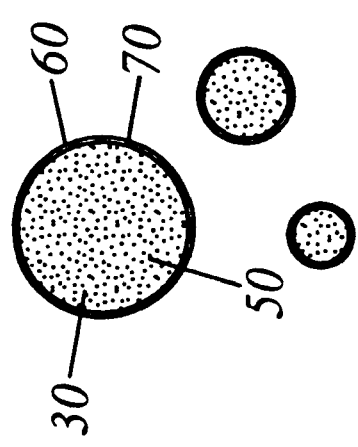
FIG. 1B shows conceptually a composite polymeric skin on certain microcapsules of the present invention.

As shown in FIG. 1A, the microcapsules 10 have an aqueous solution 30 of a bioactive substance 50 in the interior compartment 12 and have polymeric outer coatings or skins. Polymer 1 and Polymer 2 together form a rugged composite polymer membrane or shell 65, after curing. Polymer 1 primarily makes up the outermost part 60. FIG. 1B illustrates conceptually how the two polymers are thought to be distributed when the microcapsule initially forms. Polymer 1 (60) and Polymer 2 (70) are substantially distinct layers, at least initially, with Polymer 2 (70) adhering to Polymer 1 from the inside of the microcapsule and providing enhancement of the outermost membrane formed by Polymer 1.

In the present studies, large, uniformly spherical microcapsules have been prepared without using conditions of microgravity for limiting mixing between the phases. Limitation of interactions between the phases is best promoted by substantially balancing the specific gravity between the phases. By varying the density of the polymer solutions, convection can be reduced, as further described below. In either microgravity or unit gravity, using the procedures and rationale described herein, mixing between the two phases is controlled such that it is chiefly the result of diffusion-driven convection and not a function of density driven bouyancy, and fluid shear is limited to about 2–100 dynes/cm$^2$ and interfacial mixing is counteracted by the surface free energy of the respective phases.

Curing of the Membrane

Figure 8A:
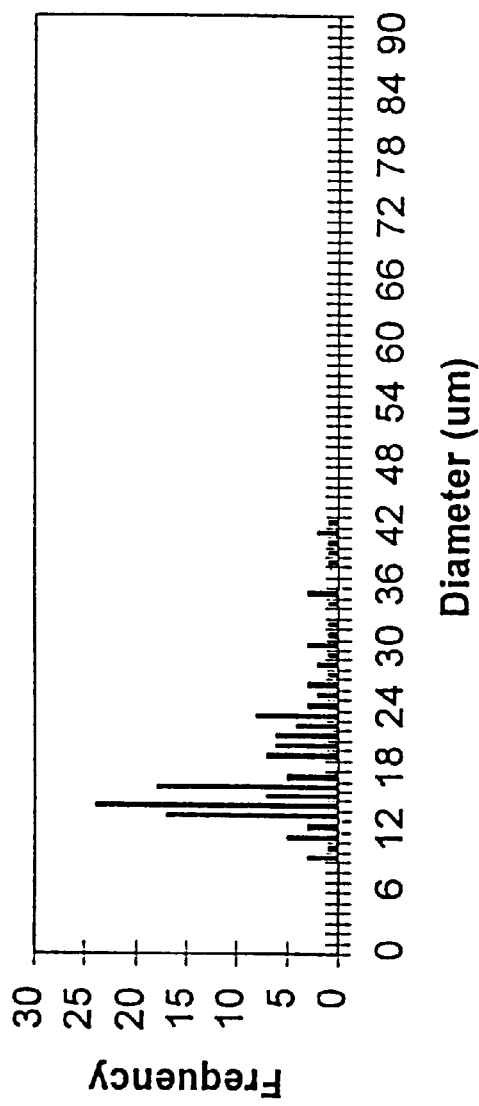
FIG. 8A is a graph showing the distribution of sizes of microcapsules containing photofrin produced by a representative method of the present invention under low shear Earth normal gravity conditions.
Figure 8B:
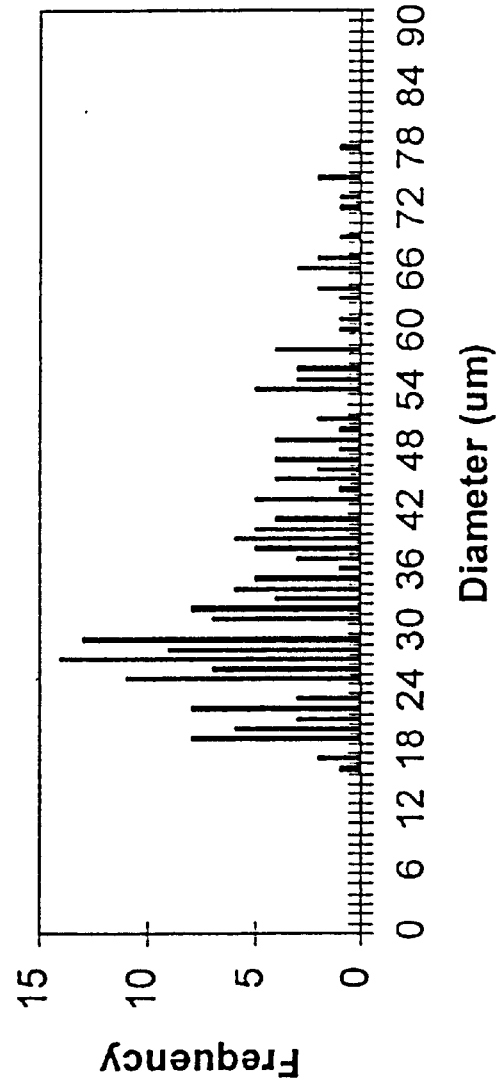
FIG. 8B is a graph showing the distribution of sizes of microcapsules containing photofrin produced by a representative method of the present invention under low shear microgravity conditions.

Studies on the Space Shuttle permitted 10 minute dispersion times followed by curing of the outer skin (exemplified by a polyglyceride) for eight days under microgravity conditions. The microcapsules formed in the microgravity environment are generally obtained in better yield and of larger average size than at Earth normal gravity, as shown in FIGS. 8A and 8B. At 1 g, a wide range of sizes generally smaller microcapsules is typically obtained. The frequency vs. size data shown in FIGS. 8A and 8B were obtained for representative microcapsules containing the drug photofrin. These microcapsules contained photofrin in the form of a saturated or nearly-saturated solution variously with or without photofrin crystals. The inventors have observed that the nature of the active material that is encapsulated can affect the resulting size range of the microcapsules.

The distribution of microcapsules obtained by a representative procedure ranges from uniform spheres of about 1 to 300 microns in diameter. By varying the formulations so as to reduce the density differential between the aqueous and organic phases, even larger microcapsures are formed, up to about 2 mm, as previously discussed. The average size of the microcapsules formed in one representative procedure, shown in FIG. 8B was about 35 microns.

The ground-based production of microcapsules is able to replicate the size range (roughly 5–250 microns in a representative study), but the average size microcapsule is typically about 10–40 microns in diameter, as shown in FIG. 8A. At least a partial reason for this wider size distribution at Earth-normal gravity is the apparent inability at 1 g to avoid certain sedimentation phenomena alone and sedimentation effects combined with weight-related contact of sedimented microcapsules. The gravity-dependent deformations of the spherical microcapsules as they form give rise to areas of thinner polymer deposition. Thus, the flexible microcapsules formed under microgravity conditions tend to have more uniform size distributions than those formed in Earth-normal gravity, are more rugged, and have a higher average diameter than ground-made microcapsules, largely due to the absence of thermal convection, buoyancy forces, and instabilities that occur at the immiscible interfaces.

These factors necessitate some additional manipulation under Earth-normal environments that is not required in the microenvironment, namely, size separation of the resulting microcapsules in order to obtain fractions of more uniform size microcapsules. Therefore, at 1 g the durability of the outer coating of the microcapsules of the present invention becomes even more important. The curing step significantly enhances the ruggedness of the Earth-normal microcapsules. An outstanding characteristic of these microcapsules is their sturdiness, as demonstrated by their ability to withstand size segregation by filtration or sieving.

The microcapsules of the present invention are equal or superior in size and function to microcapsules prepared by conventional methods. The inventors believe that there are no previously known methods of making microcapsules designed for growing a protein crystal inside the microcapsule. Due to their novel methods of making, the microcapsules prepared as described herein may have other significant features or advantages over known microcapsules that cannot be fully identified or appreciated at the present time.

EXAMPLE 2

Protein Crystallization within a Microcapsule

Figure 2:
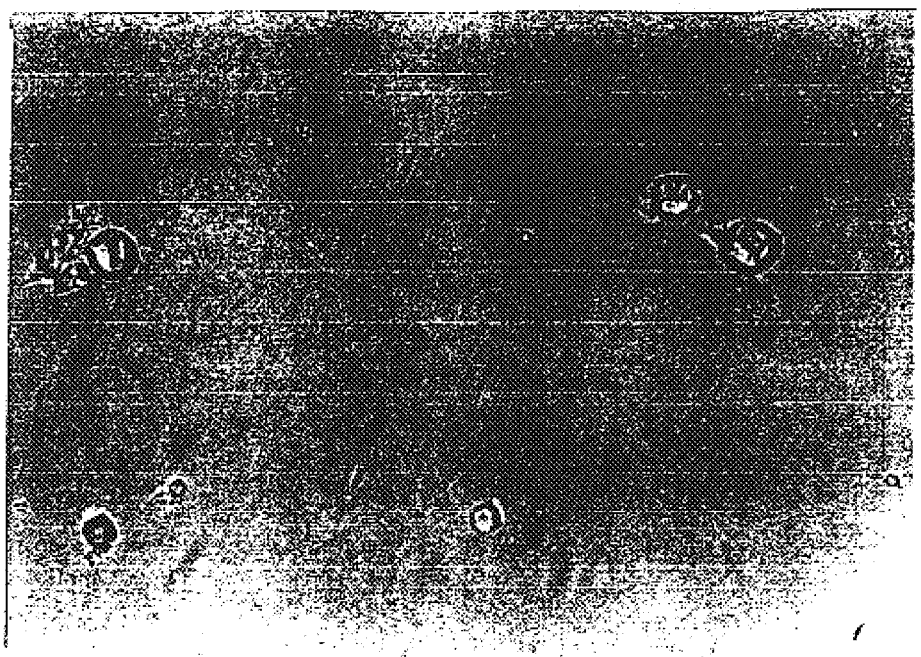
FIG. 2 is a photomicrograph of lysozyme crystals grown inside a microcapsule, formed under microgravity conditions, and having a hydrophobic, semi-permeable polymeric outer membrane in accordance with the present invention (magnification=400×).

Referring now to FIGS. 1A and 2, microcapsules containing the representative protein lysozyme were prepared essentially according to the general method described in Example 1. The Phase 2 formulation contained 7% w/v lysozyme from hen egg, and 0.01M sodium acetate, pH 4.0, dissolved in water.

In FIG. 1A, the production of microcapsules is schematically shown. Microcapsule 10 contains the Phase 2 solution 30, containing lysozyme molecules 50 in the interior cavity or compartment 12. The microcapsule initially has an outer polymeric membrane 65, made up primarily of Polymer 1, and an adherant polymeric layer 70 (FIG. 7B), which is primarily Polymer 2. After letting the microcapsules rest quiescently in the Phase 1 and Phase 2 solutions for up to about 1 hr., the outer skin 65 had fully formed and stabilized (cured) and the microcapsules are then able to withstand shear stresses equivalent to the fluid flow in a human artery, or a Reynolds number of up to about 300.

The microcapsule skin is preferably less than 1 micron thick when crystal growth within the microcapsule is of primary interest, as in the present example. When the primary goal is to place a protective, less permeable coating around a preformed crystal or to provide a carrier for a concentrated protein solution, however, a thicker polymeric skin of about 2–3 microns is preferred. The thickness of the skin may be increased, and the permeability decreased, by suspending the microcapsules in the Phase 1 solution, or in a similar alcoholic/polymer 1 solution, to apply an additional layer of polymer over the outer skin. Repeated applications will build up the skin to the preferred degree of thickness. As part of this skin thickening step, a "handle" such as an immunoglobulin-bound polymer, may be included, if desired.

Optionally, a fractionating step such as filtration or sieving, may be performed to isolate a fraction of microcapsules within a specified size range. The fluid surrounding the microcapsules was then exchanged for a dewatering fluid 120 having a higher osmotic pressure such that water molecules diffused out of the semi-permeable outer membrane. The dewatering fluid contained 25% (w/v) NaCl dissolved in deionized water. Alternatively, another similar salt could be used, at a concentration that provides an osmotic value at least 10% greater than that of the mother liquor. Similarly, a solution of 18% (w/v) higher molecular weight material such as polyethylene glycol (PEG) 8000 dissolved in deionized water may also be used for dewatering the microcapsules, or another high molecular weight PEG (of about 4–20 kDa) may be substituted.

Referring still to FIGS. 1A and 2, the higher osmotic pressure of the dewatering fluid 120 causes water molecules to diffuse out of the semi-permeable outer membrane 65 of the microcapsules, thereby dehydrating the mother liquor 35 to nucleate lysozyme crystals 55. The dewatering fluid sustains osmotic conditions that favor the growth of the lysozyme crystals within the microcapsules. The dewatering process is continued until extensive dewatering of the microcapsule is achieved, after which only a small amount of the mother liquor 35 remains and the flexible skin of the microcapsule substantially conformed to the shape of the large crystal. As can be seen in FIG. 2, the lysozyme crystal essentially fills the interior of the microcapsule. A lysozyme crystal produced in this way is of high quality, due to its large size and internal structural order. The protective skin that surrounds the mother liquor and the crystal permits the crystal to grow unperturbed by contact with a container wall or with other crystals. After completion of crystal growth, the tough, somewhat elastic, outer skin continues to protect fragile crystalline structures from breakage, and deterred penetration by the sharp crystal edges. Preferably the outer skin is about one micron or less in thickness, for obtaining optimum dewatering rates.

Figure 1C:
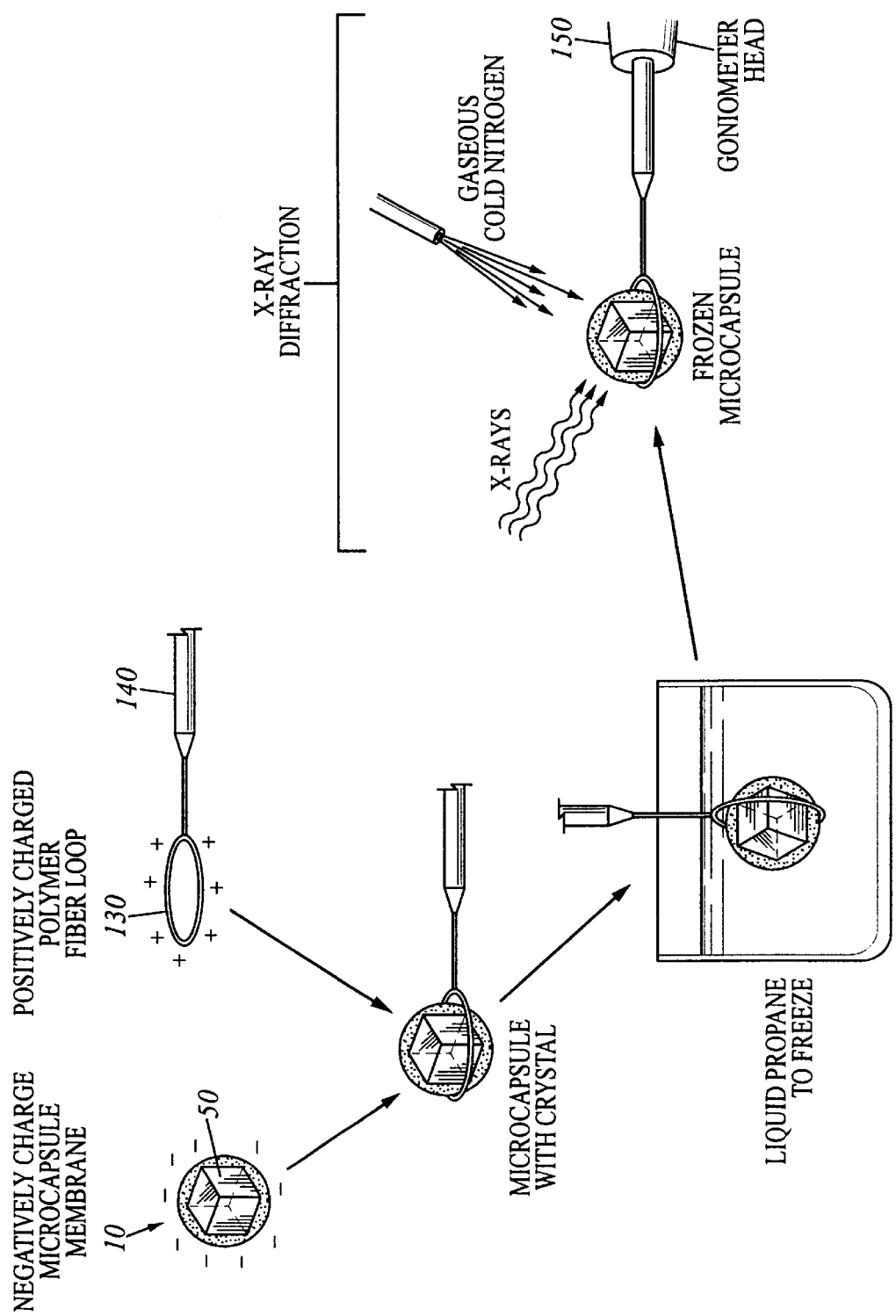
FIG. 1C shows an alternative embodiment of the microcapsules of the invention as used for x-ray crystallography.

Microcapsules containing the lysozyme crystals are conveniently harvested either by 1) suspending in a liquid carrier phase with a micropipette or 2) capturing with a hydrophobic fiber loop, preferably one having a surface charge more or less opposite that of the microcapsule. The microcapsules are then ready for analysis by polarized light microscope to determine the size and shape of the crystal(s) contained inside or mounting in an x-ray capillary tube, as illustrated in FIG. 1A. Because the crystal is bathed in mother liquor within the microcapsule, drying out of the crystal in the x-ray capillary tube is retarded or eliminated. The polymeric membrane components selected for formulating the microcapsules are selected to be transparent to x-rays and are preferably non-x-ray diffracting. FIG. 1C shows an alternative embodiment of the microcapsules of the invention as used for x-ray crystallography in a procedure that omits use of a quartz capillary tube. Use of the microcapsules for x-ray diffraction studies is discussed in more detail in Example 4, below.

This method provides distinct advantages over prior art methods of growing protein crystals by providing a closed environment which favors crystal growth under prescribed conditions of controlled dewatering. It avoids the problem of having a large crystal fall out of a hanging drop, as frequently encountered in conventional vapor diffusion methods. It also avoids having the crystal touch a container wall. In the past, typical methods employing osmotic dewatering for growing protein crystals have relied on use of small chambers having a planar reverse osmosis membrane positioned between the mother liquor and the dewatering (high osmotic pressure) salt solution. The present method uses spherical microcapsules wherein the entire outer membrane surface is available for osmotic dewatering. The spherical membrane also optimizes conditions for infiltration by hydrogen or hydroxyl ions, thereby changing the pH within the microcapsule to favor or enhance protein saturation and subsequent crystal growth. The increased surface area of the spherical microcapsule allows for more rapid change in conditions throughout the sphere of mother liquor, hence faster controlled changes all around the crystals which enhances the formation of more ordered and perfectly formed crystals.

By varying the choice and relative amounts of the Phase 1 and Phase 2 components and/or by fractionating the microcapsules, one can easily optimize the size range of the microcapsules needed for a particular protein, drug compound, or other bioactive agent. For some uses, such as in vivo drug carriers, microcapsules of 5–25 microns will be preferred. For other uses, uniform spherical microcapsules of greater than 25 microns are needed; and in still other applications such as x-ray crystallography specimens, very large 50–2000 micron crystals protected by an inert membrane covering are wanted.

FIG. 3 shows another representative protein crystal, the phytohemagglutinin concanavalin A, which was encapsulated and crystallized essentially as described for lysozyme. The aqueous phase contained 40 mg/ml ConA, 4.25 g/l sodium nitrate, 47.4 mg/l manganese chloride, 27 mg/l calcium chloride, and 43.7 mg/l TRIS acetate buffer, pH 6.5, dissolved in water. FIG. 3A shows microcapsules containing ConA crystals and mother liquor, as formed at Earth normal gravity. FIG. 3B shows the same type of microcapsules formed under conditions of microgravity on board the Space Shuttle.

The above-described procedure can be readily modified, if desired, by the encapsulation of a first phase comprised of an aqueous, near-saturated solution of protein, or other bioactive substance, and a carefully selected hydrophobic surfactant which is capable of permeating through the membrane such that the entrapped hydrophilic protein molecules become super-saturated. The super-saturated condition can be controlled such that nucleation of one or a few, well-ordered crystals occurs as the surfactant is transported through the semi-permeable "outer membrane" of the microcapsules.

Another way to enhance protein crystal formation within the microcapsules is to add a salt to the surrounding fluid As with conventional salting out procedures, any suitable non-denaturing salt such as $(NH_4)_2SO_4$ or NaCl can be used, provided that it can diffuse through the polymeric skin to cause the gradual "salting out" of the protein or it causes dewatering through the membrane.

In an alternative dewatering process, the basic method may be modified by encapsulating an aqueous near-saturated solution of protein in a semi-permeable membrane and then suspending the microcapsules in a carefully chosen dewatering fluid which, upon being subjected to a controlled electrostatic field, regulates the dewatering rate from the microcapsules by controlling the local salt concentrations on either side of the semi-permeable membrane. By controlling the concentration of protein and charged precipitant molecules at or near the surface of the growing protein crystal, the quality and size of the resulting crystal structure can be further optimized.

A suitable method and an apparatus for applying an electrostatic field to the microcapsule are disclosed in the inventors' related applications cross-referenced above. It is believed that no crystal growth-enhancing method in use today employs electrostatic fields to manipulate the local concentration of protein molecules or charged precipitant molecules near the surface of the crystal as it is growing. Although there are numerous ways of establishing an electrostatic field, one suitable apparatus is described in the inventors' related application (cross-referenced above) describing the Microcapsule and Electrostatic Processing System (MEPS) for controlling precipitant and protein concentrations inside the protective environment of the microcapsules. The disclosure of that application is incorporated herein by reference, to the extent that it provides details supplementary to those set forth herein.

The inventors have also made the surprising discovery that addition of energy in the form of uv light to the contents of the protein-containing microspheres also appears to cause a change in chemical equilibrium, producing supersaturation, crystal nucleation and acceleration of crystal growth. Ongoing investigations by the inventors are aimed at clarifying the mechanism by which this occurs.

The inventors believe that there are no previously known methods of making microcapsules designed for growing a protein crystal in the interior cavity of the microcapsule.

EXAMPLE 3

Encapsulation of a Preformed Protein Crystal and Continued Crystal Growth

Figure 5:
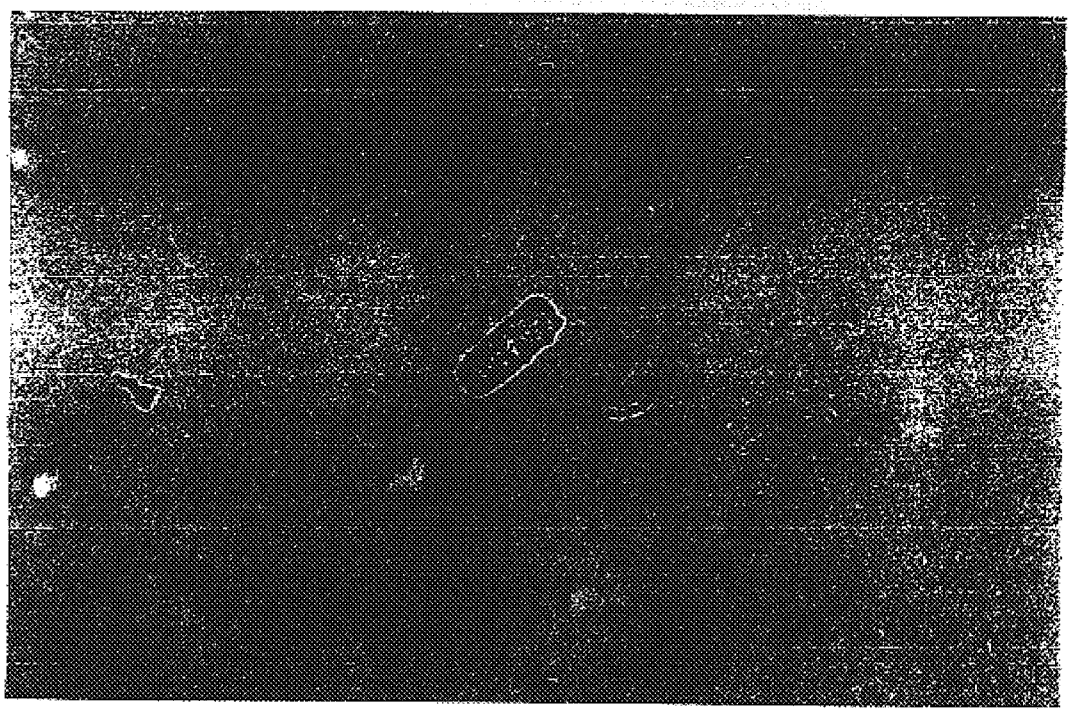
FIG. 5 is a photomicrograph of a preformed lysozyme crystal that was subsequently microencapsulated (1 g) and dewatered according to a method of the present invention, and then submersed in water (magnification=100×).

FIG. 5 is a photomicrograph taken at about 100× magnification showing a large lysozyme crystal that was encapsulated as a large preexisting crystal suspended in the Phase 2 solution, prepared as described in Example 2 and saturated or nearly saturated with dissolved lysozyme. The microcapsule was subsequently submerged in water for 12 hours prior to being photographed. It can be readily seen that the large crystal substantially fills the interior cavity and the skin around the microcapsule conforms to the shape of the crystal, with only a thin layer of mother liquor remaining between the crystal faces and the skin. The permeability of the membrane was such that the lysozyme crystal had redissolved only minimally over the 12 hour water exposure period. This establishes that the speed of water diffusion through the membrane can be limited to a very slow rate, for optimizing crystallization conditions. If desired, the microcapsule can be submerged in the alcohol/polymer 1 solution to receive an additional coating of polymer. This would provide a thicker, less permeable, more rugged polymer coat for the microcapsule, on the order of about 3–5 microns.

This demonstrates that it is possible to form sturdy membranes around existing crystals of a representative protein and thereby provide protection for even the most fragile crystals. The encapsulated crystal avoids the problem of redissolution of thin crystalline structures, typically encountered with most conventional crystal growing and handling procedures.

The microcapsules formed by the processes described in Examples 1–3 have the unique characteristic that they can be exposed to high osmotic solutions of salts, polymers, etc. which will cause dewatering of the mother liquor within the microcapsules, thereby maintaining a preexisting crystalline structure and even allowing continued crystal growth within the protective confines of the outer membrane. The present example also demonstrates that when the microcapsule has received a thicker polymer coating the microcapsule offers even more protection to the crystal, while reducing water permeability and redissolution of the crystal.

EXAMPLE 4

Crystal Preparation for X-ray Diffraction Analysis

Microcapsules containing protein crystals measuring about 50–2000 microns on a side, are prepared as described in Examples 1–3. The Polymer 1 and Polymer 2 materials chosen for use are preferably transparent to x-ray wavelengths, so as not to cause interfering diffraction patterns. The particular formulations used are optimized for formation of very large microcapsules containing a saturated or near-saturated protein solution by generating the microcapsules under conditions of very low shear field. Microcapsules containing crystals of the desired size are individually selected and carefully transferred into an x-ray capillary tube or other mount so the crystal can be orientated in a high energy x-ray beam for diffraction studies, in accordance with established methods. The encapsulated crystals are sufficiently protected by the skin of the microcapsule such that even fragile, sharp-edged crystals can be manipulated successfully into the capillary tubes.

Representative microcapsules containing large lysozyme crystals were conveniently harvested either by 1) suspending in a liquid carrier phase with a micropipette or 2) capturing with a hydrophobic fiber loop. The microcapsules were then ready for analysis by polarized light microscope to determine the size and shape of the crystal(s) contained inside or mounting in an x-ray capillary tube, as illustrated in FIG. 1A. Because the crystal is bathed in mother liquor within the microcapsule, drying out of the crystal in the x-ray capillary tube is retarded or eliminated.

As illustrated in FIG. 1C, alternatively, a microcapsule containing a large, high quality crystal is also suitable for advantageous use in an x-ray crystallography procedure that avoids the problem of manipulating a specimen into a quartz x-ray capillary tube. Such a method generally includes "lassoing" a crystal specimen, together with a drop of liquid, in a fiber loop. While the crystal is held in suspension within the loop, supported by the surface tension of the surrounding liquid, the loop is placed into liquid propane to freeze the crystal specimen. The loop is then manipulated by its handle and the handle is mounted on the goniometer head of the x-ray device. The frozen crystal, together with the associated mother liquor, is thereby situated in a continuous stream of nitrogen gas so that the crystal remains frozen while being manipulated under the x-ray beam. Referring to FIG. 1C, a microcapsule 10 containing a large crystal 55 of any desired substance, especially a protein or drug crystal, prepared as described herein, is captured, supported and manipulated by a fiber loop 130 without relying on liquid surface tension to hold the specimen in place. Not only does the sturdy, x-ray transparent membrane 65 of the microcapsule protect the fragile crystal structure while the specimen is being "teased" into the fiber loop, the polymeric skin can readily be adjusted to have an electrostatic charge on its surface. By advantageously choosing the fiber loop material and/or by applying an opposite electrostatic charge to the fiber loop, the microencapsulated crystal specimen is held in place in the loop and supported by electrostatic attraction. For example, the microcapsule membrane may have a negative charge and the polymer fiber loop may be positively charged. Some suitable fiber materials are nylon, cellulose and polyethylene terphthalate. The microencapsulated crystal specimen is then frozen and situated under the x-ray beam in the same manner as other crystals via handle 140 attached to the goniometer head 150. The new microcapsules containing large crystal specimens of 50–300 microns, and even up to about 2 mm in size, can be supported electrostatically and manipulated with the fiber loop for examination by x-ray crystallography.

EXAMPLE 5

Protein Crystal Growth between Two Solvent Phases within a Microcapsule

Figure 7:
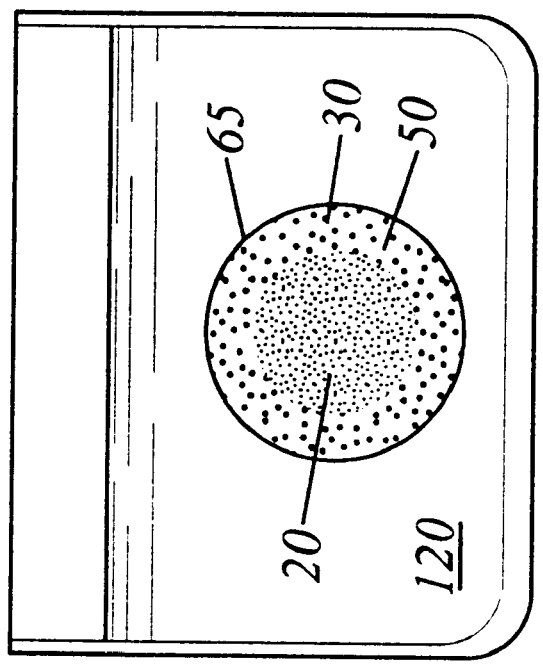
FIG. 7 is a conceptual drawing of an alternative embodiment of a microcapsule of the present invention, having a membrane surrounding an aqueous solution containing a bioactive material which itself surrounds a partially immiscible hydrocarbon core.

FIG. 7 is a conceptual drawing of a layered microcapsule made essentially as described in Examples 1–3. An aqueous saturated or nearly saturated solution of protein, or other bioactive agent (30) is encapsulated, between a non-aqueous, hydrocarbon phase (20) which is only partially miscible with the aqueous solution (30) and a third, solid phase composed of a semi-permeable polymer that forms the outer membrane (65) and which is in contact with a high osmotic concentration aqueous solution of salts or polymers (120). Dewatering from the protein solution (30) occurs by migration of water into the hydrocarbon liquid phase (20) or by transport out of through the semi-permeable membrane into the high osmotic solution (120). The particular hydrocarbon components selected for the core liquid, or hydrocarbon phase (20) are chosen based on their characteristics of being slightly miscible with water to the desired degree. This embodiment of microcapsules may be advantageous for more rapidly dewatering certain proteins or other bioactive agents.

EXAMPLE 6

Encapsulation and Crystallization of Cis-Platin

Figure 6A:
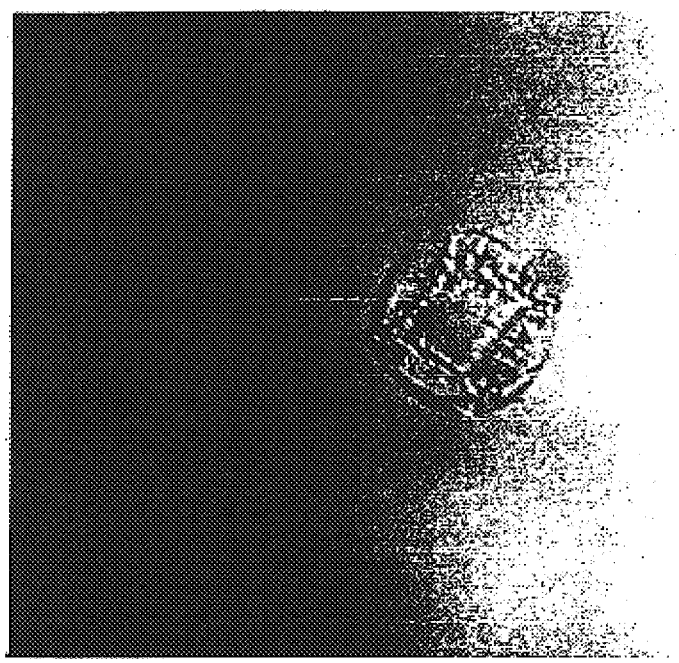
FIG. 6A is a photomicrograph of a single cis-platin crystal inside a microcapsule of the present invention containing.
Figure 6B:
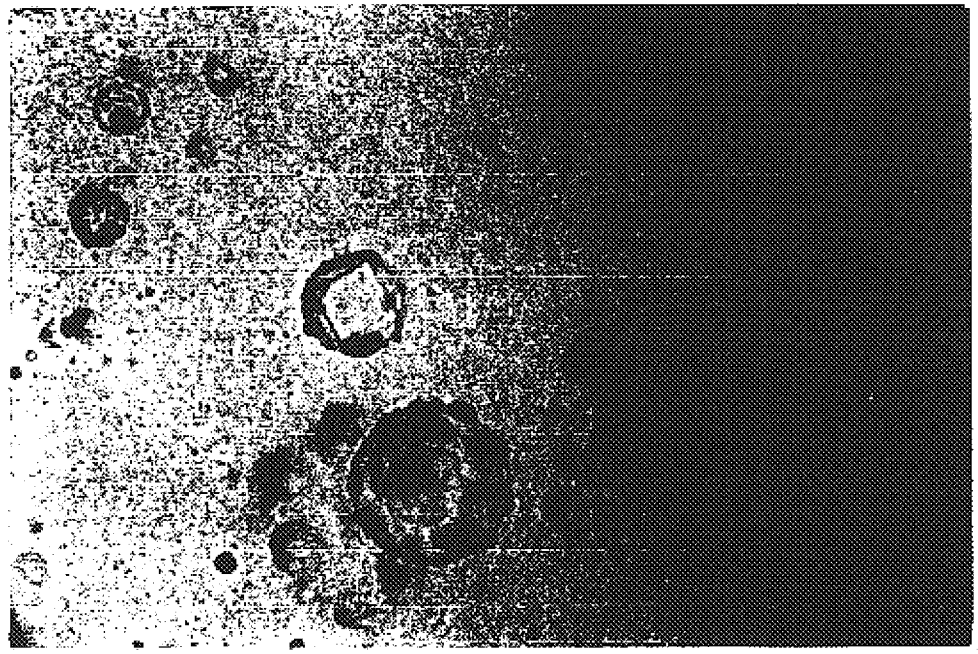
FIG. 6B is similar to FIG. 6A and shows the additional oil layer.

Referring now to FIGS. 6A and 6B, a 2% (w/v) solution of the representative pharmaceutical drug cis-platinum was microencapsulated essentially as described in Example 1, however 5% (w/v) iodinated poppy seed oil (IPO) was also included in the Phase 1 solution. The formulation is described in Table 3.

TABLE 3

| Phase 1 ("MED 10") | Phase 2 |
|---|---|
| 88.0% isopropyl alcohol | 0.2% Cis-platinum |
| 2.5% n-hexanol | 1% PEG-4000 |
| 2.5% n-heptanol | 5% Dextran-40 (MW = 40,000) |
| 5.0% IPO | 1% Sorbitan Monooleate-20 moles ethylene oxide |
| 2.0% H$_2$O | 0.8% NaCl |
| 5% w/w Glycerol Monosterin (GMS) | Balance - sterile water for injection |

This concentration of cis-platinum was sufficient to allow nascent crystal formation within the microcapsule. In this case, crystal formation occurred at or near the time of formation of the microcapsule containing the dissolved pharmaceutical material. It can readily be appreciated that the components of the aqueous solvent system used to dissolve an aqueous-soluble pharmaceutical agent may be advantageously selected, and their concentrations adjusted, to permit water molecules to migrate away from the drug-containing layer into the alcoholic mixture. The process of crystal formation is likely to be promoted in this manner after formation of the microcapsule. The results obtained in this investigation for cis-platinum is considered to be representative of other bioactive agents which can be similarly encapsulated.

Figure 4:
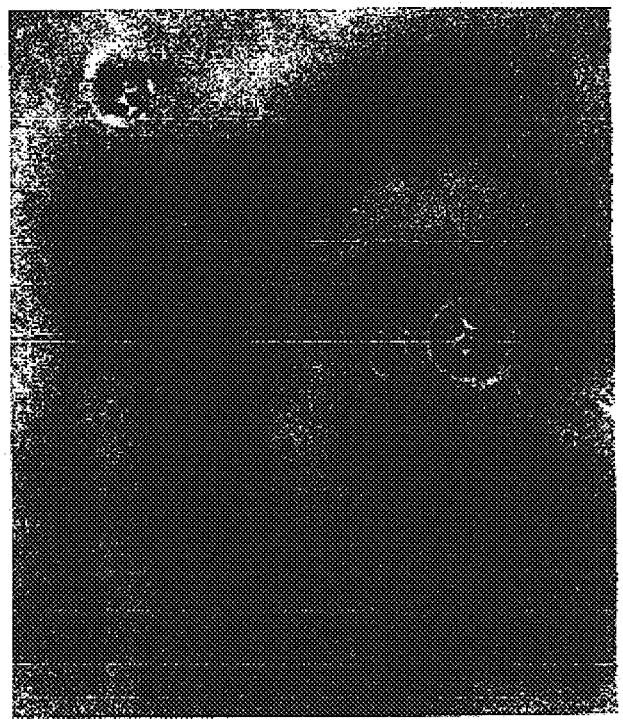
FIG. 4 is a photomicrograph of amoxicillin crystals inside a microcapsule of the present invention formed at 1 g.

Using the above-described methods, an aqueous solution of a drug or other bioactive agent which is non-saturated may be brought to super-saturation and crystal nucleation after encapsulation, via controlled transport of water out of the microcapsule's interior compartment, as described above. In this way it is possible to enhance the crystallization process after the microcapsule is formed. As shown in FIGS. 2–4, the crystal thus formed may take up most of the internal capacity of the microcapsule, i.e. about 65–90% of the internal volume.

Another representative drug, the antibiotic amoxicillin, was encapsulated essentially as described above, and the resulting microcapsule containing amoxicillin crystals and mother liquor is shown in FIG. 4.

If desired, co-encapsulation of a radio-contrast medium, as shown in FIG. 6B, enables oncologists to monitor the delivery of anti-tumor microcapsules to target tumors using computerized tomography and radiography that track the distribution of microcapsules after release from the intra-arterial catheter. Such microcapsules will have important applications in chemotherapy of certain liver, kidney, brain and other tumors.

The diameters of microcapsules possible to attain using the methods of the invention are also of particular usefulness in medical applications. Thus, whereas prior art methods have been able to routinely produce microspheres of about 1–10 micron average sizes, the present methods provide similarly-sized microcapsules of 1–20 micron diameters for intravenous administration. Also provided are 50–300 micron sized microcapsules particularly useful in interarterial chemoembolization of tumors, and microcapsules in the range of 300 micron and greater diameters useful in interperitoneal administered drugs. The membrane or skin around the outer surface of the microcapsule avoids being readily detected and largely eliminated by the reticuloendothelial system (RES). The outer skin protects the microcapsules against shear forces encountered during manufacturing processes and during transport within the vascular system enroute to the target tissues. The hydrophobic outer membrane can also be modified, by selection of advantageous polymeric and/or non-polymeric components, so as to retard oxygen transport and thereby reduce oxidative degradation of the entrapped drug. This would likely improve the shelf-life of parenteral suspensions. The flexible, deformable outer skin on the microcapsules of the invention provides increased packing densities within vascular beds. This results in microcapsules superior to prior art solid microspheres (e.g. gelatin, albumin or starch) commonly used for chemoembolization therapy against tumors. It is expected that the new microcapsules, carrying more concentrated amounts of drugs which are already known to be therapeutically effective, will be even more effective as substitutes for existing liposome encapsulated drugs. The thin, semi-permeable membrane of some embodiments of the new microcapsules permits controlled release of the encapsulated drug at the desired site of action. Since the concentration of drug in a microcapsule and its release rate are easily determined, the correct microcapsule dosage for a particular drug can be calculated from the customary dosages for that drug.

As another option, the polymeric skin may be made initially insoluble in Phase 2 but slowly solubilizable in physiological body fluids (e.g., blood, serum, plasma, extracellular fluid, saliva, mucus). Alternatively, sustained or controlled release at a therapeutic target site may be obtained by modifying the above-described method to provide a somewhat thinner, drug-semi-permeable membrane on the microcapsule. Upon injecting into a person in need of the drug, the microcapsules serve to protect tissues, arterioles and veins from the sharp edges of the drug crystals.

While the preferred embodiment of the invention has been shown and described, modifications thereof can be made by one skilled in the art without departing from the spirit and teachings of the invention. For example, a saturated non-aqueous solution of a drug could also be similarly encapsulated and then exposed to conditions which would remove solvent through the outer membrane, producing a similar supersaturated condition, crystal nucleation and/or acceleration of the drug crystal growth, within a microcapsule. The embodiments described herein are exemplary only, and are not limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

REFERENCES

Allen, T. M., Mehra, T., Hansen, C. and Chin, Y. C., "Stealth Liposomes: An Improved Sustained Release System for 1-b-D-Arabinofuranosylcytosine," Cancer Res. 52:2431–39, 1992.

Barenolz, Y. and Haran, G., "Method of Amphiphatic Drug Loading in Liposomes by pH Gradient," U.S. Pat. No. 5,192,549, issued Mar. 9, 1993.

Carter, Daniel C., "Apparatus for Mixing Solutions in Low Gravity Environments," U.S. Pat. No. 4,909,933, issued Mar. 20, 1990.

Carter, Daniel C., "Protein Crystal Growth Tray Assay," U.S. Pat. No. 5,130,105, issued Jul. 14, 1992.

Martin, et al. "Microreservoir Liposome Composition and Method," U.S. Pat. No. 5,225,212, issued Jul. 6, 1993.

Todd, P., Sidkar, S. K., Walker, C. and Korszun, Z. R., "Application of Osmotic Dewatering to the Controlled Crystallization of Biological Macromolecules and Organic Compounds," J. Crystal Growth 110: 283–292 (1990).

Willoughby et al., "Neutral Glycolipid as an Adsorbent for Enteric Viral Pathogens," U.S. Pat. No. 5,192,551, issued Mar. 9, 1993.

Woodle, et al. "Liposomes with Enhanced Circulation Time," U.S. Pat. No. 5,013,556, issued May 7, 1991.

What is claimed is:

1. An improved method of determining the three-dimensional structure of a predetermined protein molecule by x-ray crystallography including mounting a crystal in an x-ray capillary tube and subjecting said crystal to a high energy x-ray crystallographic procedure to obtain a characteristic x-ray diffraction pattern of said protein crystal, wherein the improvement comprises:

forming a microcapsule containing a saturated or near saturated aqueous solution of said protein surrounded by a semi-permeable polymeric membrane;

exposing said microcapsule to a dewatering solution having a higher osmotic pressure than said encapsulated protein solution whereby water is osmotically removed from said encapsulated protein solution;

controlling the concentration of a dewatering agent in said dewatering solution such that gradual, ordered crystallization of said protein occurs within said microcapsule;

growing said crystal to at least about 50–300 microns;

harvesting the resulting crystal-containing microcapsule;

selecting a microcapsule containing a crystal of sufficient size and crystalline quality for obtaining an x-ray diffraction pattern.

2. An improved method of determining the three-dimensional structure of a predetermined protein molecule by x-ray crystallography including isolating a crystal specimen of said protein in a fiber loop, freezing said crystal specimen, mounting said crystal specimen and fiber loop on a goniometer head such that said crystal is positioned in a continuous cold $N_2$ stream loop and kept frozen, and rotating said goniometer in an x-ray beam, wherein the improvement comprises substituting for said crystal specimen a microencapsulated crystal comprising a protective outer membrane surrounding an interior cavity, said interior cavity containing a saturated or nearly saturated solution of a protein and containing a crystal of said protein substantially filling said interior cavity, said membrane being transparent to the x-ray beam.

3. The method of claim 2 wherein said membrane comprises an electrostatic charge such that said microencapsulated crystal is electrostatically attracted to said loop, said electrostatic attraction being sufficient to support said microencapsulated crystal inside said loop.

4. The method of claim 2 wherein a drop of liquid is adhered to the outer membrane of said microencapsulated crystal.

5. The method of claim 2 wherein the outer membrane of said microcapsule is negatively charged and said loop comprises a fiber having a positive electrostatic charge.

6. The method of claim 2, wherein said fiber is nylon, cellulose or polyethylene terphthlate.

7. The method of claim 2, wherein said crystal of said protein is a highly ordered structure.

8. The method of claim 2, wherein said fiber has a surface charge opposite that of said microcapsule.

* * * * *